United States Patent [19]

Park et al.

[11] Patent Number: 4,919,933
[45] Date of Patent: Apr. 24, 1990

[54] METHOD FOR THE TREATMENT OF DENTAL DISEASE

[76] Inventors: Hae-chul Park; Young-cha Choi; Kyung-dong Park; Mi-ae Park; Kyu-dong Park, all of 144-16, Wooam-dong, Chungju-si, Choongbuk-do, Rep. of Korea

[21] Appl. No.: 269,591

[22] Filed: Nov. 10, 1988

[51] Int. Cl.$^5$ .................... A61K 32/20; A61K 35/04
[52] U.S. Cl. .................................. 424/196.1; 424/680
[58] Field of Search ............ 424/49, 58, 195.1, 196.1, 424/680, 196.1

[56] References Cited

U.S. PATENT DOCUMENTS

| | | | |
|---|---|---|---|
| 71,407 | 11/1867 | Payne | 424/468 |
| 125,492 | 4/1872 | Shannon | 424/195.1 |
| 129,469 | 7/1872 | Gaddy | 424/196.1 |
| 202,231 | 4/1878 | Childs | 424/196.1 |
| 209,879 | 11/1878 | French | 424/195.1 |
| 281,521 | 7/1883 | Kingzett et al. | 424/196.1 |
| 302,761 | 7/1884 | Moore | 424/195.1 |
| 333,361 | 12/1885 | Ulrici | 424/196.1 |
| 380,700 | 4/1888 | Schwartz | 424/58 |
| 624,925 | 5/1899 | Grapewine | 424/58 |
| 1,073,725 | 9/1913 | Yeganian | 424/58 |
| 1,136,613 | 4/1915 | Raub | 424/196.1 |
| 1,370,263 | 3/1921 | Babb | 424/196.1 |
| 1,379,744 | 5/1921 | Congreve | 424/49 |
| 1,968,858 | 8/1934 | Sheffield et al. | 424/49 |
| 2,024,146 | 12/1935 | Crowther | 424/49 |
| 2,291,205 | 7/1942 | Borglin | 424/196.1 |
| 2,658,851 | 11/1953 | Brandenberger | 424/49 |
| 4,374,824 | 2/1983 | Wahml | 424/58 |
| 4,812,306 | 3/1989 | Cocherell et al. | 424/58 |

FOREIGN PATENT DOCUMENTS

| | | | |
|---|---|---|---|
| 1133831 | 10/1982 | Canada | 424/58 |
| 2657896 | 7/1978 | Fed. Rep. of Germany | 424/58 |
| 2533437 | 3/1984 | France | 424/58 |
| 81816 | 6/1980 | Japan | 424/196.1 |
| 126412 | 8/1982 | Japan | 424/58 |
| 2067 | of 1858 | United Kingdom | 424/196.1 |
| 4117 | of 1886 | United Kingdom | 424/196.1 |

*Primary Examiner*—Shep K. Rose
*Attorney, Agent, or Firm*—Banner, Birch, McKie & Beckett

[57] ABSTRACT

A composition and method of use for the treatment of pain and inflammation associated with dental disease is disclosed. The composition comprises pine resin and salt in a 1:1–5 parts by weight relationship which is prepared by mixing the pine resin and salt, heating the mixture while stirring, cooling and grinding the resulting solid to a powder form.

3 Claims, No Drawings

METHOD FOR THE TREATMENT OF DENTAL DISEASE

FIELD OF THE INVENTION

The present invention relates to a composition and method of use for the treatment of dental disease. More specifically, the composition comprises pine resin and table salt (sodium chloride) which are mixed, heated and ground to form a powder for the treatment of dental caries and periodontitis.

INFORMATION DISCLOSURE STATEMENT

Several therapeutic measures and methods have been used for the prevention and treatment of dental disease, especially dental caries. In the severe cases tooth extraction may be the only remedy.

There is a need to prevent or treat dental disease at a lower cost with the effective alleviation of any associated dental pain.

Therefore, it is an object of this invention to provide a topical composition which aids in the treatment of pain and inflammation associated with dental and gum disease. It is a further object of this invention to provide a topical composition which aids in preventing dental disease by applying, at least daily, the composition of the invention to a patient not suffering from a disease in the oral cavity which may exhibit inflammation and pain. It is a further object of this invention to provide a method of relieving pain and inflammation associated with dental caries by applying an effective amount of the composition of the invention to the involved dental area of a patient suffering from pain and inflammation associated with dental caries. The foregoing has outlined some of the more pertinent objects of the present invention. These objects should be construed to be merely illustrative of some of the more pertinent features and applications of the invention. Many other beneficial results can be obtained by applying the disclosed invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying examples.

SUMMARY OF THE INVENTION

The composition and methods of use of the present invention are defined by the appended claims with specific embodiments shown in the examples. For the purpose of summarizing the invention, the invention relates to a composition for the treatment of dental disease which provides an excellent and immediate effect for the prevention and treatment of pain and inflammation associated with dental disease such as dental caries. The composition consists essentially of pine resin and table salt (sodium chloride) in a specific relationship.

More particularly, the composition comprises a mixture of pine resin and table salt in a ratio of about 1:1 to 5, parts by weight, respectively, which is prepared by mixing pine resin and table salt in the ratio mentioned above, heating the mixture while stirring, cooling to room temperature, and grinding the resulting solid to a powder form.

The composition may further include a pharmaceutically acceptable excipient(s) which are therapeutically inert but aid in the preparation of a pharmaceutical preparation. Such excipients include sweeteners, slow release agents, flavoring agents, preservatives, diluents or the like which are known to these skilled in the art of formulating pharmaceutical preparations.

The invention further includes a method of treating dental caries by applying an effective amount of a composition comprising pine resin and sodium chloride in a ratio of about 1:1-5, parts by weight, respectively, to the involved dental area of a patient suffering from dental caries.

Preferably, the composition consists essentially of pine resin and sodium chloride.

The invention further includes a method of preventing inflammation and pain associated with dental disease in the oral cavity of a patient not suffering from a disease in the oral cavity which exhibits inflammation and pain by topically applying to the teeth and associated areas within the oral cavity which may exhibit inflammation and pain an effective amount of a composition comprising pine resin and sodium chloride in a ratio of about 1:1-5, parts by weight, respectively, which are mixed, heated and ground to form a powder. Preferably, the composition is applied daily to aid in preventing inflammation and pain associated with dental disease in the oral cavity.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other compositions for carrying out the same purposes of the present invention. It should also be realized by those skilled in the art that such equivalent constructions do not depart from the spirit and scope of the invention as set forth in the appended claims.

DETAILED DESCRIPTION

The composition of the present invention is prepared by mixing natural pine resin obtained from a pine tree and table salt in a ratio of about 1:1 to 5 parts by weight, then heating the mixture slowly while stirring well to allow the pine resin to be melted, then cooling to room temperature and grinding the resulting solid to a fine powder.

The pine resin component of the present invention is readily obtainable from a stem or trunk of the pine tree. Pine resin has been used in medicine for a long time and is considered to be harmless to the human body.

Pinus rigida, more widely known as the pitch pine tree, is most preferred as a source of the pine resin. The resin is collected from the tree's natural release of the resin through the bark of the tree where it forms in beads or drops which are removed for use in the composition. Pinus rigida grows in many parts of the world including Korea and North America.

Other species of pine would be expected to provide a resin useful in the instant invention. Such pines would include the white pine, Norway pine, and the like.

When an appropriate amount of the present composition is applied to (inserted into) the affected area, e.g. dental caries, a portion of the composition enters the cavity. After a few minutes, the affected area may be washed with water. Onset of a decrease in dental pain is usually rapidly exhibited with one application. The amount of composition necessary to achieve the benefits of the invention is determined by the area to be contacted by the composition. In applying the composition to a cavity, only a small amount, such 2-15 mg is needed to fill the cavity. Practically speaking a larger amount is used to contact the area proximate the cavity and the cavity itself in order to ensure delivery of a therapeutic amount to the cavity or involved area.

The prevention of dental disease is exhibited when an appropriate amount of the present composition is employed when brushing the teeth and the area proximate the teeth, e.g. gums. Further, the effect for preventing dental disease means that a patient having a medical history of dental disease does not suffer from the disease to the extent he suffered without the use of the composition of the invention. Preferably, the composition of the invention is applied daily by brushing or the like.

The dental disease treated herein includes various diseases of the oral cavity, for example, dental caries, periodontitis, and the like, which manifest themselves by dental pain and inflammation.

According to an experimental test of the present invention, either table salt or pine resin was applied to patients with dental caries. In this test, the analgesic effect lasted only for 2 to 3 minutes. On the other hand, the composition according to the present invention surprisingly obtained a dramatic therapeutic effect without recurrence of the disease as indicated by pain and inflammation for about three to six months and longer.

In addition, in the case where dental pain recurs after the first application of the present composition, the composition of the present composition is applied again (about two or three times) which usually provides relief from the dental pain. Thereafter there is usually no further recurrence of the disease as indicated by the absence of pain upon daily treatment of the involved area with the composition of the invention.

The following examples are presented to illustrate in detail the present invention. The pharmacologically active components, pine resin and sodium chloride when combined as indicated, of this invention can be processed in accordance with conventional methods of galenic pharmacy to produce a medicinal agent for topical application to patients, including e.g., mammals or humans suffering from dental disease such as dental caries.

EXAMPLE 1

1 g of pine resin obtained from pine tree (pinus rigidia) is mixed with 4 g of table salt in powder (finely ground) form in a vessel. The mixture is heated slowly to allow the pine resin to melt while stirring well. Heating of the mixture should be carefully watched and the mixture should not be heated for over about twenty minutes.

When decoloration appears and the resulting product becomes hardened (crisp), heating is stopped. The product is cooled to room temperature and then ground to a fine powder similar in appearance to powdered sugar. The product is placed into a container for storage and maintained in a dry state.

EXAMPLE 2

To the composition obtained from Example 1 a pharmaceutically acceptable excipient, such as dextran, is added and the mixture is processed and formed into slow releasing granules and tablets. Such methods are known to those skilled in the art of pharmaceutical formulations. Preferably, the amount of excipient necessary is the minimum amount required to accomplish its purpose. This ensures the least possible dilution of the active ingredients.

If necessary, for children a sweetner which is nontoxic is added to the dental disease.

EXAMPLE 3

To a patient with dental caries a single and small cavity and manifesting severe dental pain, about 2-15 mg of the composition of Example 1 is applied to the affected area.

To another patient with dental caries a single and small cavity and manifesting the same painful symptom about 2-16 mg of the composition of Example 1 is pressed placed into a scrap of cloth and applied to the affected area so as to be positioned on the affected area.

Another patient having dental caries a single and small cavity with the same painful symptom about 2-15 mg of the granules of Example 2 is applied to the involved area.

The result of the above clinical tests was very satisfactory. Namely, a remarkable analgesic effect is exhibited usually within about 5 to 10 minutes. Furthermore, only after the application of the present composition over 2 or 3 times there was no recurrence for at least 6 months.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A method of preventing inflammation and pain associated with dental disease in the oral cavity of a patient not suffering from disease in the oral cavity which exhibits inflammation and pain by topically applying to the teeth and associated areas within the oral cavity which may exhibit inflammation and pain an effective amount of a composition consisting essentially of pine resin and table salt in a ratio of about 1:1 to 5 parts by weight, respectively, and which is prepared by mixing pine resin and table salt in the ratio mentioned above, heating the above mixture while stirring, cooling the mixture to room temperature, and grinding the resulting solid to a powder form.

2. A method of relieving pain associated with dental caries by applying to the involved dental area of a patient suffering from pain associated with dental caries an effective amount of a composition consisting essentially of pine resin and table salt in a ratio of about 1:1 to 5 parts by weight, respectively, and whic is prepared by mixing pine resin and table salt in the ratio mentioned above, heating the above mixture while stirring, cooling the mixture to room temperature, and grinding the resulting solid to a powder form.

3. The method of claim 1 wherein the composition is applied daily.

* * * * *